United States Patent [19]

Vali et al.

[11] Patent Number: 5,179,028
[45] Date of Patent: Jan. 12, 1993

[54] ANTIBODY COATED CRYSTAL CHEMICAL SENSOR

[75] Inventors: Victor Vali, Laguna Hills; Kenn S. Bates, Long Beach; David B. Chang, Tustin; Brian M. Pierce, Moreno Valley, all of Calif.

[73] Assignee: Hughes Aircraft Company, Los Angeles, Calif.

[21] Appl. No.: 511,707

[22] Filed: Apr. 20, 1990

[51] Int. Cl.$^5$ .................. G01N 33/551; G01N 30/96; H01L 41/04; H01L 41/08

[52] U.S. Cl. .................................. 436/524; 436/501; 436/806; 436/908; 422/68.1; 422/69; 422/82.01; 310/312; 310/323; 310/341; 310/370; 73/DIG. 4

[58] Field of Search ............... 204/403; 436/501, 908, 436/806, 524; 422/82.01, 88, 98, 69, 68.1; 73/61 R, 24.03, DIG. 4; 310/312, 323, 341, 370

[56] References Cited

U.S. PATENT DOCUMENTS

| | | | |
|---|---|---|---|
| 1,875,953 | 9/1932 | Taylor | 310/341 |
| 3,037,174 | 5/1962 | Bommel et al. | 310/341 |
| 3,071,736 | 1/1963 | Vonbun et al. | 310/341 |
| 3,553,602 | 1/1971 | Brothers et al. | 310/341 |
| 3,673,872 | 4/1972 | Ensley | 73/505 |
| 4,415,827 | 11/1983 | Chuang | 310/370 |
| 4,498,025 | 2/1985 | Takahashi | 310/370 |
| 4,668,331 | 5/1987 | Ostriker | 156/620.71 |
| 4,735,906 | 4/1988 | Bastiaans | 436/501 |
| 4,789,804 | 12/1988 | Karube et al. | 422/57 |
| 4,905,701 | 3/1990 | Cornelius | 436/806 |

FOREIGN PATENT DOCUMENTS 0576332 1/1932 Australia .

OTHER PUBLICATIONS

"Immobilization Methods for Piezoelectric Biosensors," Bio/Technology, vol. 7, Apr. 1989, pp. 349-351.

Primary Examiner—James C. Housel
Assistant Examiner—Jan M. Ludlow
Attorney, Agent, or Firm—Wanda K. Denson-Low; Michael W. Sales

[57] ABSTRACT

A sensor for detecting the presence of a particular chemical by determining the absolute frequency shift in the oscillating frequency of an antibody-coated oscillator. Specific antibodies deposited on a high Q crystal oscillator detect the change in frequency as chemical particulates become trapped by the antibodies and change the effective mass of the crystal. In one embodiment, two oscillating crystals are used, one that has been coated with the antibodies, and one that is uncoated. This permits detection of frequency differences between the oscillating frequencies of the two crystals, thus eliminating pressure, temperature, and humidity corrections that conventionally must be made. The sensor maintains a high specificity by using antibodies that are specifically related to the chemical to be detected, while achieving relatively good sensitivity by using high Q oscillators, such as quartz or sapphire, and eliminating drift problems due to temperature, pressure, and humidity. In a second embodiment, a single crystal is used having antibodies coated at specific nodal locations associated with harmonics of the fundamental frequency of oscillation of the crystal. Harmonic amplitudes are measured to determine the presence of the chemical of interest.

5 Claims, 2 Drawing Sheets

FUND = λ/4

3RD HARMONIC = 3λ/4

ANTIBODY COATED CRYSTAL CHEMICAL SENSOR

BACKGROUND

The present invention relates generally to chemical sensors, and more particularly, to a chemical sensor that employs antibody coated oscillators.

There exists a need for chemical sniffers that have high selectivity, low false signal rate, and high sensitivity, on the order of one part in $10^8-10^9$. Sensitive chemical detectors are desired for drug and contraband detection, and explosives detection, including plastic explosives and dynamite. Additionally, chemical sensors may be used in the environmental cleanup and hazardous material field. Chemical detectors exist that are highly specific, including devices such as spectrum analyzers, for example, but such devices have relatively low sensitivity levels. Chemical detectors also exist that are very sensitive, but these are not specific enough to one chemical (low selectivity), thus increasing false signal rates.

Dr. George Guilbault, at the University of New Orleans, has experimented with coating quartz crystal oscillators with antibodies. His research is discussed in a paper entitled "Immobilization Methods For Piezoelectric Biosensors," published in *Bio/Technology*, Vol. 7, April 1989, pages 349-351. However, these oscillators must be corrected for temperature, pressure, and humidity. The experiments must be done in a laboratory because of sensitive corrections that are required. These corrections result in a decreased sensitivity in such devices.

Accordingly, it would be an advantage in the chemical detection art to have a detector that is both selective and highly sensitive and that may be employed outside controlled laboratory conditions.

SUMMARY OF THE INVENTION

The present invention employs specific antibodies deposited on a high Q crystal oscillator to cause the change in frequency when particulates that the antibodies are specific to become trapped by the antibodies. The trapped particulates change the effective mass of the crystal and hence change the oscillating frequency thereof. In particular, two crystals are used, one that has been coated with the antibodies, and one that is uncoated. This permits detection of the absolute frequency difference between the oscillating frequencies of the coated oscillator, before and after exposure to the chemical.

Specific antibodies deposited on the crystal oscillator detect the change in frequency as chemical particulates become trapped by the antibodies and change the effective mass of the crystal. Two oscillating crystals are used, one that has been coated with the antibodies, and one that is uncoated. This permits detection of frequency differences between the oscillating frequencies of the two crystals, thus eliminating pressure, temperature, and humidity corrections that conventionally must be made.

An alternative embodiment of the present invention employs a mass loading technique that only allows the chemical particulates to adsorb onto the crystal in specific nodal locations of a harmonic of the primary frequency. The ratio of the amplitudes of the harmonics are then measured. This technique may be used with the two crystal approach, or because of the stability of this ratio under changing temperature, pressure, and humidity conditions, may be used without the uncoated reference crystal. However, more complex scanning electronic circuitry is required to locate the peaks (shifting in frequency).

The chemical sensor of the present invention maintains a high specificity by using antibodies which are specifically related to a particular chemical, such as TNT, DNT, cocaine or marijuana, for example. The sensor achieves relatively good sensitivity by using two high Q oscillators and also eliminates drift problems due to temperature, pressure and humidity that typically occur with conventional sensors. Additionally, the present chemical sensor is rugged and is able to fit in a small package, whereas many conventional sensors will not.

A variety of crystal oscillators, including quartz and sapphire may be used. Furthermore, the crystals may be cooled to liquid helium temperature, which substantially increases the Q of quartz by a factor of over ten. Also, the use of an out-of-phase scheme for each crystal oscillator and integrating from minimum to maximum permits the possibility of reaching the photon noise limit.

BRIEF DESCRIPTION OF THE DRAWINGS

The various features and advantages of the present invention may be more readily understood with reference to the following detailed description taken in conjunction with the accompanying drawings, wherein like reference numerals designate like structural elements, and in which.

DETAILED DESCRIPTION

Biologically produced molecules that bind with specific molecules, including DNT, TNT, marijuana and cocaine, for example, are called antibodies. There are two types of antibodies: monoclonal and polyclonal. Monoclonal antibodies only interact with specific molecules and may be used to obtain high specificity. Polyclonal antibodies bind to several related molecules, including DNT and TNT, for example. Antibodies currently exist for DNT, TNT, marijuana, cocaine, and other chemicals of interest. A surface covered with antibodies may typically bind with up to $10^{13}$ molecules/cm$^2$.

Figure 1A:
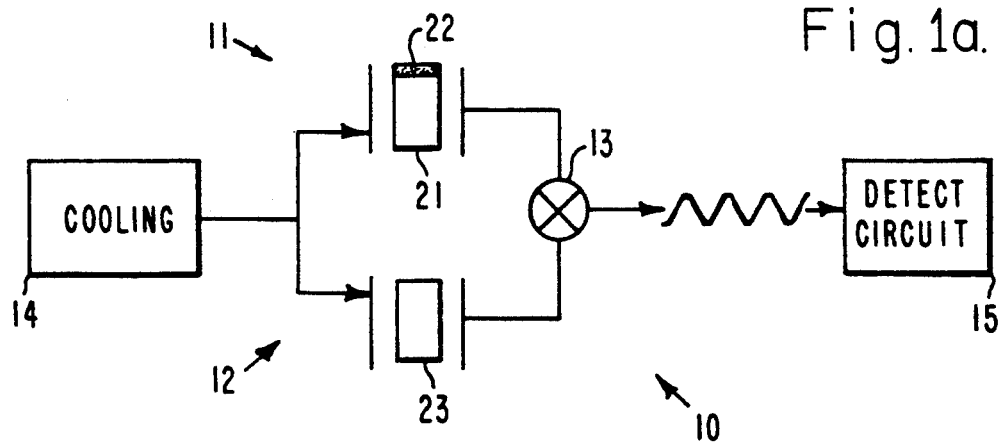
FIGS. 1a and 1b illustrate an antibody coated dual crystal chemical sensor in accordance with the principles of the present invention.
Figure 1B:
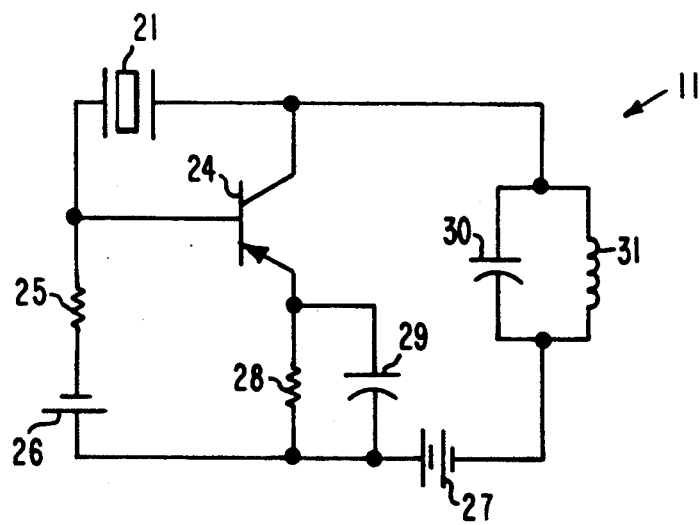

With reference to FIGS. 1a and 1b, an antibody coated dual crystal chemical sensor 10 in accordance with the principles of the present invention is shown. The sensor 10 comprises a coated piezoelectric crystal oscillator circuit 11, one example of which is the circuit shown in FIG. 1b. The coated piezoelectric crystal oscillator circuit 11 may be comprised of a coated piezoelectric crystal 21 made of a material such as quartz, or sapphire, for example, having its outer surface coated with either polyclonal or monoclonal antibodies 22. Typical polyclonal or monoclonal antibodies 22 may be employed to bind molecules of chemicals comprising DNT and TNT, for example. Antibodies for TNT, DNT, morphine and other chemicals are available from IRT Corporation in San Diego.

A second substantially identical crystal oscillator circuit 12 comprising an uncoated crystal 23 is disposed adjacent to the first oscillator circuit 11. Outputs of the two circuits 11, 12 are coupled to a frequency mixer 13, for example, that is adapted to mix the output signals from the two oscillator circuits 11, 12 to produce a detectable beat frequency signal. Cooling of the crystals 21, 23 may be provided by cooling apparatus 14, such as a cryogenic refrigerator, for example. The beat frequency signal output from the mixer 13 is coupled to a detection circuit 15 that is adapted to process the beat frequency signals to produce a signal indicative of the detection of a chemical of interest.

With reference to FIG. 1, the two crystal oscillators 21, 23 are part of the respective crystal controlled oscillator circuits 11, 12 that are adapted to control the oscillating frequencies thereof such that they oscillate at substantially the same frequency. The electronics associated with the crystal controlled oscillator circuits 11, 12 are generally well known, and each may comprise the oscillator circuit 11 shown in FIG. 1b, for example. The oscillator circuit 11 shown in FIG. 1b includes the coated crystal 21, a transistor 24 having its collector and base coupled across the crystal 21 and wherein the base is coupled by way of a resistor 25 and capacitor 26 in series to the positive terminal of a voltage source 27. The emitter of the transistor 24 is coupled by way of a resistor 28 and capacitor 29 in parallel to the positive terminal of the power source 27. Finally, the negative terminal of the power source 27 is coupled through a capacitor 30 and inductor 31 in parallel to the collector of the transistor 24.

Figure 2:
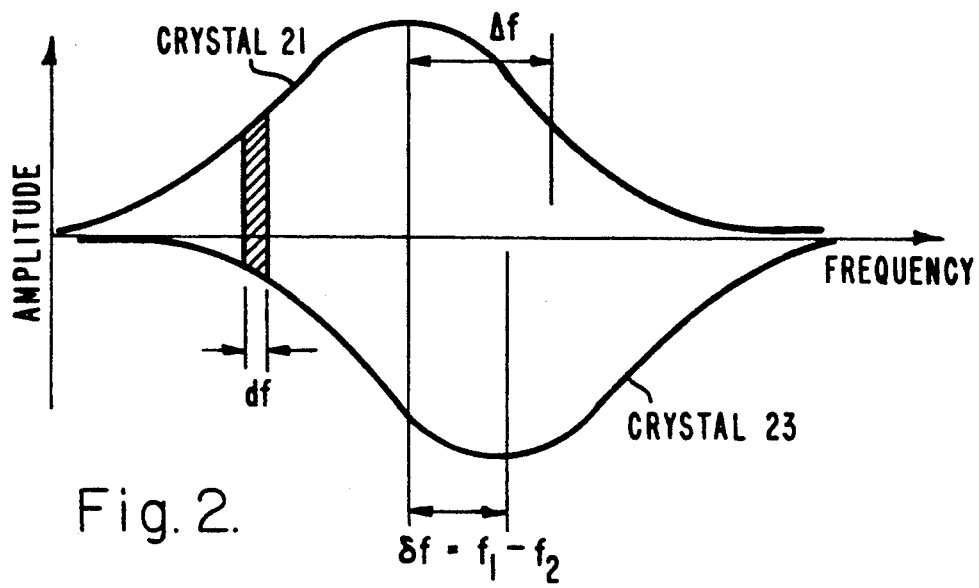
FIG. 2 shows curves illustrating an out-of-phase detection scheme that may be employed with the sensor of FIG. 1.

With reference to FIG. 2, the second uncoated crystal oscillator 23 acts as a control for the coated crystal oscillator 21, in that it provides reference data for frequency computations made on the coated crystal oscillator 21. The two crystal oscillator circuits 11, 12 are also coupled to the detection circuit 15 that is adapted to detect the oscillating frequencies of each of the crystal oscillators 21, 23 and produce a signal indicative of the frequency difference between the frequency of oscillation of the first crystal oscillator 21 before and after exposure to a chemical of interest that the antibodies 22 are adapted to adsorb.

In operation, the crystal oscillator 21 is exposed to air or water contaminated with a chemical that is to be detected. The mass increase of chemical particulates bound by the antibodies 22 on the coated crystal oscillator 21 is detected through a frequency shift of the output signals from the coated oscillator 21. The frequency shift is given by the equation $\Delta f/f = -\frac{1}{2}\Delta m/m$, where f is the frequency of oscillation of the coated oscillator 21, $\Delta f$ is the change in frequency after exposure to the chemical of interest, m is the mass of the coated oscillator 21 and $\Delta m$ is the change in mass of the coated oscillator 21 resulting from adsorption of the chemical by the antibodies 22 on the surface thereof.

Quartz crystal oscillator normal mode frequencies, for example, range from $10^4$ to about $5 \times 10^7$ Hz. A 0.1 mm thick disc of quartz has a $f_0 = 2 \times 10^7$ Hz, and has higher order harmonics of up to $2 \times 10^8$ Hz. The Q of a quartz crystal is quite high and may be greater than or equal to $10^6$.

The mass of the maximum amount of the chemical adsorbed by the first crystal oscillator 21 is given by the equation $\Delta m = n \times M \times m_H$, where n is the added molecule density ($10^{13}$ molecules/cm$^2$), M is the molecular weight of the absorbed molecule, and $m_H$ is the mass of a hydrogen atom. For a material such as TNT, for example, where $M \approx 220$; $\Delta m \approx (10^{13}$ molecules/cm$^2) \times (220$ molecule$^{-1}) \times (1.7 \times 10^{-24}$ grams$) = 3.7 \times 10^{-9}$ gm/cm$^2$. A quartz crystal disc having a 0.1 mm thickness has mass $m \approx 0.01$ cm$\times 2.2$ grams/cm$^3 = 0.022$ gm/cm$^2$. Therefore, the frequency shift for the coated crystal oscillator 21 made of quartz and having an operating frequency of $f = 20$ MHz is $\Delta f = (-\frac{1}{2}\Delta m/m)f = (-\frac{1}{2})(3.7 \times 10^{-9}$ gm/cm$^2/2.2 \times 10^{-2}$ gm/cm$^2)/(2 \times 10^7$ Hz$) = 1.7$ Hz.

This magnitude of sensitivity is somewhat difficult to measure due to temperature, pressure and humidity changes that affect the absolute vibrational frequency of the crystal oscillators 21, 23. In accordance with the principles of the present invention, by employing two crystal oscillators 21, 23, and having the first crystal oscillator 21 coated with antibodies 22 and the second crystal oscillator 23 as a reference, $\Delta f$ may be measured by detecting the beat frequency between the two crystal oscillators 21, 23. The sensor may be electronically nulled to ignore the mass of the antibody alone, without any adsorbed chemical particulates. There is an uncertainty ($\delta$) in the beat frequency, and for $f = 2 \times 10^7$ and $Q \approx 1.3 \times 10^7$, is given by: $\delta(\Delta f) \approx f/Q = 1.5$ Hz.

However, this uncertainty may be substantially reduced by increasing the Q of the coated crystal oscillator 21, thus making the measurement easier. The Q of the coated crystal oscillator 21 may be increased by the following techniques. The coated crystal oscillator 21 may be cooled to liquid helium temperature, as illustrated in FIG. 1a by the cooling apparatus 14, such as a cryogenic refrigerator, for example. Cooling of the crystal oscillators 21, 23 substantially increases the Q of quartz by a factor of over ten. A crystal oscillator that has a substantially higher Q, such as sapphire, may be employed. Also, an out-of-phase detection scheme may be employed for each of the crystal oscillators 21, 23 which comprises integrating the output frequency signals from each of the crystal oscillators 21, 23 during the measurement period from minimum to maximum, which increases the probability of reaching the photon noise limit.

The details of the out-of-phase scheme are as follows, and shall be described with reference to FIG. 2. It is possible to increase the detection capability of $\delta f = (f_1 - f_2)$ of the detection circuit 15 beyond its Q determined bandwidth. The two crystal controlled oscillators 21, 23 have similar (almost identical) Q are operated in opposite phase as illustrated in FIG. 2. The Fourier components in the first half of the resonance curve will produce a net charge (N) in the detection circuit 15. The charge (N) is proportional to the recording time. There is, however, a statistical noise equal to $N^{\frac{1}{2}}$ associated with the random distribution of the number of electrons, commonly referred to as shot noise. Therefore, the accuracy of determining the best frequency is proportional to the square root of time.

Specifically the number of charges $N_1$ and $N_2$ produced by the oscillators 21, 23 in a frequency interval df is given by:

$$N_1(f)df = \frac{Btdf}{(f-f_1)^2 + (\Delta f)^2} \pm \sqrt{N(f)dt}$$

$$N_2(f)df = \frac{Btdf}{(f-f_2)^2 + (\Delta f)^2} \pm \sqrt{N_2(f)dt}$$

where $\Delta f$ is the line width of the oscillation, t is the measurement time, $\sqrt{Ndt}$ is Poisson noise on the signal $N(f)df$, and B is a constant. The difference is given by $D(f)df = (N_1 - N_2)df$. If $df < \delta f < < \Delta f$, where $df = f_2 - f_1$, to get $D(f)df > 2\sqrt{N_1(f)df}$, and $$\sqrt{Bt} > \frac{1}{\sqrt{dt}} \frac{\Delta f}{\delta f} \frac{8}{3}$$

It is therefore possible to detect partial covering of the antibody surface with the chemical of interest.

The number of molecules n collected per unit area by the antibody covered surface is $n = n_g v \xi t$ where $n_g$ is the number density of the molecules in air, v is the thermal velocity, $\xi$ is the sticking coefficient and t is the time. Numerically, for TNT and DNT, their molecular weights are about 200 and $v = 2 \times 10^4$ cm/sec at room temperature. Therefore, to collect $10^{13}$ molecules per square centimeter, the time required is $t \approx 50/\xi$ seconds, and where $\xi$ is one of the quantities to be determined.

The dual crystal chemical sensor 10 employing an antibody-coated crystal oscillator 21 in accordance with the present invention is a very sensitive device. It is sensitive enough to detect the presence of the cited chemicals when the surface of the coated crystal oscillator 21 is only partially covered with the respective chemical. Furthermore, for some antibodies the reaction is reversible, thus allowing repeated use of the same coated crystal oscillator 21 for sensing different chemicals.

Figure 3:
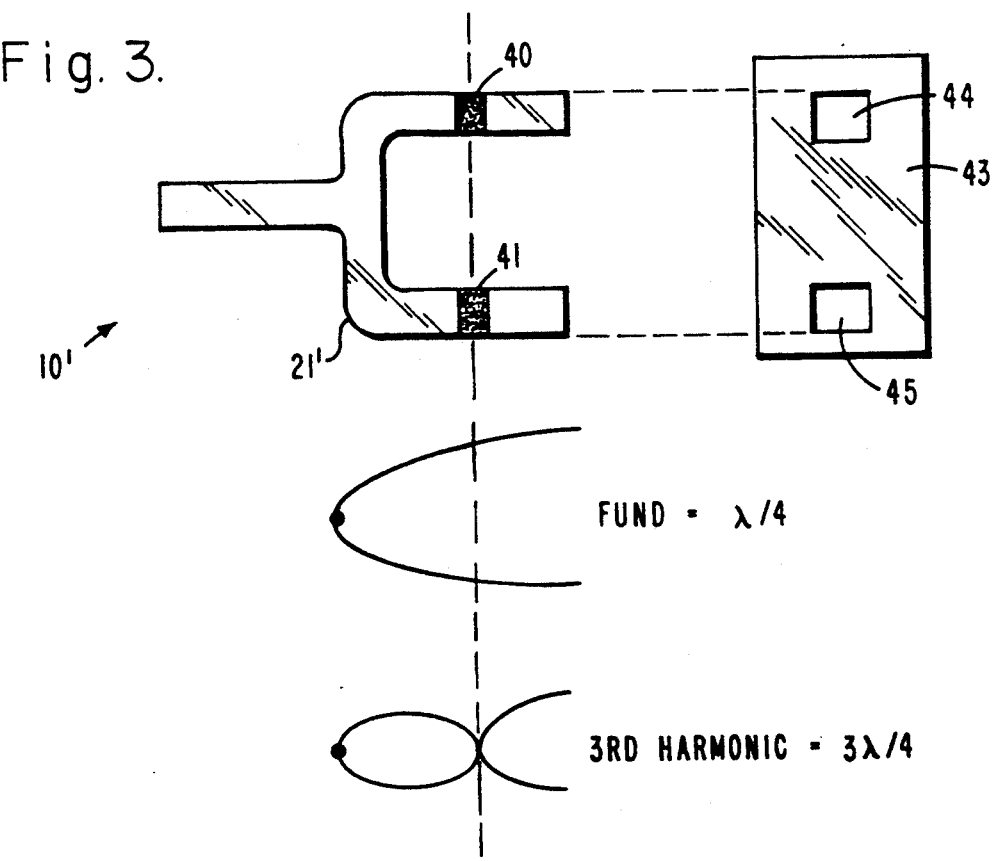
FIG. 3 shows a second embodiment of a sensor in accordance with the principles of the present invention.

A second embodiment of the sensor 10' of the present invention is shown in FIG. 3 and employs the use of a mass loading of the chemical to be detected at specific locations 40, 41 on the crystal oscillator 21'. The crystal oscillator 21' is shown configured in the shape of a tuning fork. There is, however, no restriction to the use of tuning-fork shaped oscillator crystal shown in FIG. 3, for clearly, other shaped crystals may be used. These locations 40, 41 are chosen to correspond to nodal locations for a particular higher frequency but a non-nodal location for the fundamental. By restricting the chemical under detection to only these locations 40, 41 by: (1) only coating the antibodies 22 at these locations 40, 41; (2) placing a baffle 43 above the crystal oscillator 21 (shown in phantom to the right of the oscillator 21' in FIG. 3 with windows 44, 45 located above the locations 40, 41) which only allows exposure in the desired locations 40, 41 or (3) both (1) and (2).

The advantages gained by the sensor 10' of FIG. 3 is that the ratio of the $N^{th}$ harmonic to the fundamental (or a lower harmonic than the Nth) is detected. This ratio is independent of temperature and pressure. Therefore it is only necessary to measure the change in amplitude ratio of the harmonics of the sensor 10' of FIG. 3.

Figure 4A:
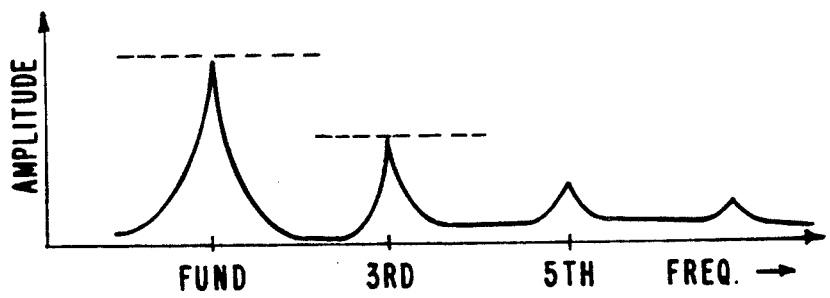
FIGS. 4a and 4b show a chemical detection scheme using the sensor of FIG. 3.
Figure 4B:
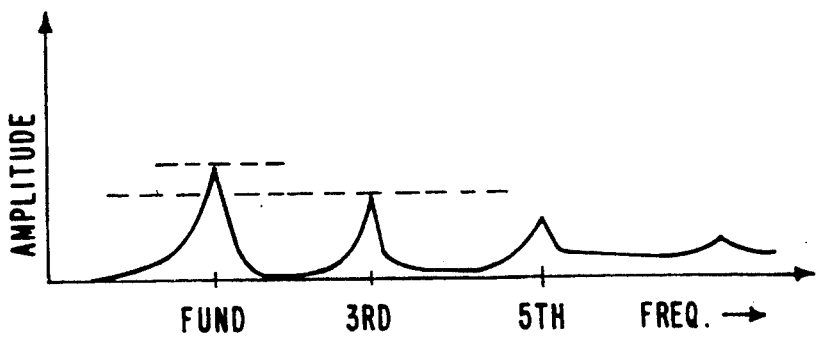

FIGS. 4a and 4b show detection spectra generated using the sensor 10' shown in FIG. 3. FIG. 4a shows the detected spectrum without the presence of any chemical to be detected. FIG. 4b shows the same spectrum with the detectable chemical adsorbed on the surface of the coated crystal oscillator 21 of the sensor 10'. The mass loading reduces the lower harmonic frequency oscillating amplitude. The resolution may be read out by detecting the ratio of the harmonics chosen, illustrated in FIG. 4b as the first and third harmonic.

Because a ratio of the harmonic amplitudes are measured instead of absolute frequencies, a single coated crystal oscillator 21 may be employed without the reference crystal oscillator and still achieves the temperature, pressure, and humidity insensitivity. However using a reference crystal oscillator with the coated crystal oscillator 21' allows for simpler detection electronics to be used.

Thus there has been described new and improved chemical sensors that employ antibody coated oscillators. It is to be understood that the above-described embodiments are merely illustrative of some of the many specific embodiments which represent applications of the principles of the present invention. Clearly, numerous and other arrangements can be readily devised by those skilled in the art without departing from the scope of the invention.

What is claimed is:

1. A chemical sensor for detecting the presence of predetermined chemical particles in the vicinity of said sensor, said sensor comprising:
   an antibody-coated crystal oscillator for providing a measurement signal;
   an uncoated crystal oscillator for providing a reference signal; and
   detecting means coupled to the oscillators for receiving the signals from the coated and uncoated oscillators and determining the difference between the signals to provide an indication of the presence of predetermined chemical particles in the vicinity of the sensor wherein the coated crystal has antibodies located at specific nodal locations corresponding to the nodes of higher harmonic frequencies, and such that the predetermined chemical particles attach only substantially at the specific nodal locations.

2. The chemical sensor of claim 1 wherein the coated sensor has antibodies coated thereon only near the specific nodal locations.

3. The chemical sensor of claim 1 wherein the coated sensor has baffles disposed adjacent thereto that cause chemical particles adsorbed thereby to adsorb only near the specific nodal locations.

4. A chemical sensor for detecting the presence of predetermined chemical particles in the vicinity of said sensor, said sensor comprising:
   a crystal oscillator having antibodies located at specific nodal locations corresponding to the nodes of higher harmonic frequencies, and such that the predetermined chemical particles attach only substantially at the specific nodal locations; and
   detecting means coupled to the oscillator for detecting the harmonic amplitudes of the oscillator caused by adsorption of chemical particles by the antibodies on the oscillator, which determination provides an indication of the presence of predetermined chemical particles in the vicinity of the sensor.

5. The chemical sensor of claim 4 wherein the crystal oscillator has the shape of a tuning fork.

* * * * *